United States Patent
Si et al.

(10) Patent No.: US 12,393,057 B2
(45) Date of Patent: Aug. 19, 2025

(54) OLEIC ACID-RELEASING CONTACT LENS

(71) Applicant: CooperVision International Limited, Fareham (GB)

(72) Inventors: Erwin C. Si, Alameda, CA (US); Nancy J. Keir, Pleasanton, CA (US); Subam Basuthkar Sundar Rao, San Ramon, CA (US); Victoria Rogers, Pleasanton, CA (US); Yuan Ji, San Jose, CA (US); Yuwen Liu, Dublin, CA (US); Hyo Jeang Lee, Pleasanton, CA (US)

(73) Assignee: COOPERVISION INTERNATIONAL LIMITED, Fareham (GB)

( * ) Notice: Subject to any disclaimer, the term of this patent is extended or adjusted under 35 U.S.C. 154(b) by 945 days.

(21) Appl. No.: 17/529,305

(22) Filed: Nov. 18, 2021

(65) Prior Publication Data

US 2022/0187620 A1    Jun. 16, 2022

Related U.S. Application Data

(60) Provisional application No. 63/125,419, filed on Dec. 15, 2020.

(51) Int. Cl.
| | |
|---|---|
| G02C 7/04 | (2006.01) |
| A45C 11/00 | (2006.01) |
| A61K 9/00 | (2006.01) |
| B29D 11/00 | (2006.01) |
| G02B 1/04 | (2006.01) |
| B29K 105/00 | (2006.01) |

(52) U.S. Cl.
CPC .............. *G02C 7/04* (2013.01); *A45C 11/005* (2013.01); *A61K 9/0048* (2013.01); *B29D 11/00067* (2013.01); *B29D 11/00125* (2013.01); *G02B 1/043* (2013.01); *B29K 2105/0002* (2013.01)

(58) Field of Classification Search
CPC ....... G02C 7/04; A45C 11/005; A61K 9/0048; B29D 11/00125; G02B 1/043; B29K 2105/0002
See application file for complete search history.

(56) References Cited

U.S. PATENT DOCUMENTS

| | | | |
|---|---|---|---|
| 4,168,112 | A | 9/1979 | Ellis et al. |
| 6,867,245 | B2 | 3/2005 | Iwata et al. |
| 7,426,993 | B2 | 9/2008 | Coldrey et al. |
| 8,231,218 | B2 | 7/2012 | Hong et al. |
| 8,388,995 | B1 | 3/2013 | Ali et al. |
| 8,658,747 | B2 | 2/2014 | Liu et al. |
| 8,865,789 | B2 | 10/2014 | Yao et al. |
| 11,945,180 | B2 * | 4/2024 | Alli .................. B29D 11/00192 |
| 2004/0039077 | A1 | 2/2004 | Baba et al. |
| 2005/0074497 | A1 | 4/2005 | Schultz |
| 2006/0012751 | A1 | 1/2006 | Rosenzweig et al. |
| 2007/0035693 | A1 | 2/2007 | Back |
| 2008/0124376 | A1 | 5/2008 | Pruitt et al. |
| 2008/0152540 | A1 | 6/2008 | Schorzman et al. |
| 2009/0258070 | A1 | 10/2009 | Burnier et al. |
| 2010/0140114 | A1 | 6/2010 | Pruitt et al. |
| 2011/0306661 | A1 | 12/2011 | Sato et al. |
| 2012/0026457 | A1 | 2/2012 | Qiu et al. |
| 2012/0172486 | A1 | 7/2012 | Zhu et al. |
| 2013/0005691 | A1 | 1/2013 | Gallois-Bernos |
| 2013/0335697 | A1 | 12/2013 | Smith et al. |
| 2014/0174962 | A1 | 6/2014 | Luk et al. |
| 2014/0285765 | A1 | 9/2014 | Fujisawa et al. |
| 2018/0355112 | A1 | 12/2018 | Zhang et al. |
| 2019/0022046 | A1 | 1/2019 | Zhu et al. |

FOREIGN PATENT DOCUMENTS

| | | |
|---|---|---|
| CN | 101238403 A | 8/2008 |
| CN | 101534793 A | 9/2009 |
| CN | 102597854 A | 7/2012 |
| CN | 106675394 A | 5/2017 |
| CN | 107022287 A | 8/2017 |
| CN | 110756131 A | 2/2020 |
| EP | 3373047 A1 | 9/2018 |
| JP | 860156706 A | 8/1985 |
| JP | 2020528565 A | 9/2020 |
| KR | 20170125126 A | 11/2017 |
| TW | 201517938 A | 5/2015 |
| TW | 201906596 A | 2/2019 |

(Continued)

OTHER PUBLICATIONS

Combined Search and Examination Report issued in corresponding United Kingdom Patent Application No. GB2117784.5 dated May 25, 2022 (9 pages).
International Preliminary Report On Patentability issued in corresponding International Patent Application No. PCT/GB2021/053223 mailed Sep. 14, 2022 (13 pages).
Search Report issued in corresponding Chinese Patent Application No. 202180037934.0 dated Jul. 3, 2023 (5 pages).
Taiwan Notice of Allowance with Search Report issued in corresponding Taiwan Patent Application No. 110144950 dated Jan. 9, 2024 (6 pages).
Search Report issued in corresponding United Kingdom Patent Application No. GB2117784.5 dated Feb. 28, 2024 (2 pages).
Office Action issued in corresponding Japanese Patent Application No. 2022-577288 mailed May 25, 2023 (with English translation)(4 pages).

(Continued)

*Primary Examiner* — Zohreh A Fay
(74) *Attorney, Agent, or Firm* — Kilyk & Bowersox, P.L.L.C.

(57) ABSTRACT

An oleic acid-releasing contact lens is described as well as method of manufacturing the same. The oleic acid-releasing contact lens contains oleic acid releasably adhered to the polymeric lens body, and releases from 2 μg to 25 μg oleic acid after 1 hour in a release media. The oleic acid-releasing contact lens can be comfortably worn by a symptomatic contact lens wearer, and can increase the duration of comfortable lens wearing time and/or reduce lens awareness events in a symptomatic contact lens wearer.

14 Claims, No Drawings

(56) References Cited

FOREIGN PATENT DOCUMENTS

WO 2013024857 A1 2/2013
WO 2021211670 A1 10/2021

OTHER PUBLICATIONS

Chalmers et al., "Contact Lens Dry Eye Questionnaire-8 (CLDEQ-8) and Opinion of Contact Lens Performance," Optometry and Vision Science, Oct. 2012, vol. 89, No. 10, pp. 1435-1442.
Read et al., "Monitoring ocular discomfort using a wrist-mounted electronic logger," Contact Lens and Anterior Eye, (2020) https://doi.org/10.1016/j.clae.2020.02.010.
Torres-Luna et al., "Extended delivery of cationic drugs from contact lenses loaded with unsaturated fatty acids," European Journal of Pharmaceutics and Biopharmaceutics, Oct. 1, 2020, vol. 155, pp. 1-11.
International Search Report and Written Opinion issued in corresponding International Patent Application No. PCT/GB2021/053223 mailed Mar. 16, 2022 (14 pages).

\* cited by examiner

OLEIC ACID-RELEASING CONTACT LENS

This application claims the benefit under 35 U.S.C. § 119(e) of prior U.S. Provisional Patent Application No. 63/125,419, filed Dec. 15, 2020, which is incorporated in its entirety by reference herein.

FIELD OF THE INVENTION

The field of the invention relates to contact lenses, and particularly, to contact lenses that are more comfortable for symptomatic contact lens wearers.

BACKGROUND OF THE INVENTION

An estimated 50% of all contact lens wearers experience discomfort while wearing their lenses, and approximately 25% of these symptomatic contact lens wearers permanently discontinue wearing lenses. Sensations of lens awareness is a primary reason for contact lens dissatisfaction in symptomatic contact lens wearers. Despite advances in contact lens materials, there remains a need for improved contact lenses that can be comfortably worn by contact lens wearers who otherwise experience sensations of lens awareness while wearing contact lenses that are currently commercially available.

The cornea is the most densely innervated tissue in the body and is exclusively innervated by A-delta and C primary afferent fibers. The C nerve fibers are non-myelinated; and while the A-delta fibers are slightly myelinated, they lose their myelin sheath after they enter the cornea to keep cornea transparent. Thus, both types of nerve fibers have their nerve terminals exposed when they reach the squamous layer of the cornea. Located on these nerve terminals are receptors for sensing temperature, chemical, pain, and touch. The pain receptor (nociceptor) that is shown to be present on these nerve terminals is TRPV1.

SUMMARY OF THE INVENTION

A feature of the present invention is to provide a hydrogel contact lens that can release oleic acid during lens wearing.

An additional feature of the present invention is to provide a contact lens that can be comfortably worn by a symptomatic contact lens wearer.

An additional feature of the present invention is to increase the duration of comfortable lens wearing time and/or reduce lens awareness events in a symptomatic contact lens wearer.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention, in part relates to a hydrogel contact lens containing an amount of oleic acid releasably adhered to the lens that enhances the comfort of the contact lens in a symptomatic lens wearer and/or increases the duration of comfortable contact lens wearing time in a symptomatic contact lens wearer. In one example, the hydrogel contact lens is a silicone hydrogel contact lens comprising a polymeric lens body that is a reaction product of a polymerizable composition for a non-silicone hydrogel that includes at least one acyclic tertiary amine monomer.

In one example, the silicone hydrogel contact lens is capable of releasing 2 μg to 25 μg oleic acid after 1 hour in an in vitro release media comprising 30 vol % ethanol in phosphate buffered saline.

Furthermore, the present invention relates to a method of making the silicone hydrogel contact lens of the present invention. The method includes the steps of a) polymerizing a polymerizable composition (as described herein) in a contact lens mold to obtain a polymeric lens body, b) removing the polymeric lens body from the contact lens mold, c) extracting the polymeric lens body in an organic solvent comprising from about 500 ppm to about 2000 ppm oleic acid, d) hydrating the polymeric lens body in a hydration liquid to obtain the silicone hydrogel contact lens, e) sealing said silicone hydrogel contact lens with packaging solution in a package, and e) autoclaving said package.

Furthermore, the present invention relates to a method of correcting the vision of a symptomatic contact lens wearer by providing to a symptomatic contact lens wearer an oleic acid-releasing silicone hydrogel contact lens, wherein the oleic acid-releasing hydrogel contact lens contact lens increases the duration of comfortable contact lens wearing time and/or reduces lens awareness events in the symptomatic contact lens wearer compared to a control lens that does not contain oleic acid.

Furthermore, the present invention relates to the use of an oleic acid-releasing hydrogel contact lens by a symptomatic contact lens wearer that wears an initial contact lens that does not contain oleic acid for four or more hours and replaces the initial contact lens with an oleic acid-releasing hydrogel contact lens to increase end-of-day comfort of the symptomatic contact lens wearer.

DETAILED DESCRIPTION

Hydrogel contact lenses that release oleic acid during wear and their method of manufacture are described herein. The contact lens can be referred to, herein, as an oleic acid-releasing contact lens. Oleic acid, which is a TRPV1 antagonist, is released from the lens during wear in amounts that enhance the comfort of contact lens wear in symptomatic contact lens wearers, and can increase the duration of time in which a symptomatic contact lens wearer can comfortably wear contact lenses. In particular, the oleic acid-releasing lens of the invention can increase the end-of-day comfort of lens wear in symptomatic patients.

The oleic acid releasing contact lens comprises a polymeric lens body and an amount of oleic acid releasably adhered to the polymeric lens body. As one example, the contact lens is a reaction product of a polymerizable composition for a non-silicone hydrogel. Non-silicone hydrogel contact lenses are typically formed from polymerization of one or more hydrophilic monomers such as 2-hydroxyethyl methacrylate (HEMA) or vinyl alcohol, optionally in combination with other monomers, and contains no siloxane molecule.

As an example, the contact lens comprises a polymeric lens body that is the reaction product of a polymerizable composition comprising at least one siloxane monomer and at least one hydrophilic monomer and/or at least one hydrophilic polymer. Conveniently, as described in more detail below, a cured polymeric lens body for a silicone hydrogel may be extracted in an extraction solvent containing the oleic acid which results in the desired amount of oleic acid adhering to the polymeric lens body. The oleic acid may be adhered to the polymeric lens body by cationic and/or hydrophobic interaction, and/or may be physically entrapped by the polymer network of the polymeric lens body. Alternatively, or additionally, the oleic acid may be added to the polymerizable composition.

The amount of oleic acid "releasably adhered" to the polymeric lens body refers to the total amount of oleic acid that can be extracted from the contact lens by an isopropyl alcohol (IPA) extraction method as described in Example 1 below. In one example, the amount of oleic acid releasably adhered to the polymeric lens body can be at least about 25 µg, or 50 µg, up to about 150 µg, 250 µg, or 500 µg, such as about 100 µg to about 300 µg. As used herein, and unless context dictates otherwise, a reference to an amount of oleic acid released from the oleic acid-releasing contact lens over a specified duration of time or to a "release profile" of the oleic acid, refers to the amount of oleic acid released from the lens as measured using the in vitro release media (30 vol % EtOH in PBS) and method described in Example 3 below. In one example, the cumulative amount of oleic acid released from the contact lens after one hour in the release media is between 2 µg to 25 µg oleic acid, or between 7 µg to 20 µg oleic acid or from 2 µg to 18 µg oleic acid or from 2 µg to 15 µg oleic acid, or from 2 µg to 10 µg oleic acid, or from 5 µg to 12 µg oleic acid. In another example, the contact lens has an oleic acid release profile wherein a total of 2 µg to 10 µg oleic acid is released at 30 minutes (cumulative), a total of 7 µg to 20 µg oleic acid is released at 1 hour (cumulative), a total of 15 µg to 45 µg oleic acid is released at 3 hours (cumulative), a total of 25 µg to 65 µg oleic acid is released at 6 hours (cumulative), and a total of 35 µg to 75 µg oleic acid is released at 9 hours (cumulative). In one example, the contact lens has a sustained release profile wherein about 3 µg to about 20 µg oleic acid is released per hour for at least 8 hours or at least 9 hours. Sustained release profiles can be achieved when the polymeric lens body has charged groups that facilitate uptake of the oleic acid, prevent burst release of the oleic acid from the contact lens, and extend the duration of oleic acid release from the lens. A "burst release" of more than about 12 µg oleic acid within 30 minutes after lens insertion may result in stinging or discomfort. Accordingly, in one example, the oleic acid-releasing contact lens releases less than 10 µg or less than 8 µg oleic acid in 30 minutes (when tested using the in vitro release method of Example 3).

The polymeric lens body may comprise any hydrogel material suitable for use as a contact lens material. A silicone hydrogel material for contact lenses is typically formed by curing a polymerizable composition (i.e. a monomer mixture) comprising at least one siloxane monomer and at least one hydrophilic monomer or at least one hydrophilic polymer, or a combination thereof. As used herein, the term "siloxane monomer" is a molecule that contains at least one Si—O group and at least one polymerizable group. Siloxane monomers used in contact lens compositions are well-known in the art (see, e.g., U.S. Pat. Nos. 8,658,747 and 6,867,245). (All patents and publications mentioned here and throughout are incorporated in their entirety by reference.) In some examples, the polymerizable composition comprises a total amount of siloxane monomer of at least 10 wt. %, 20 wt. %, or 30 wt. % up to about 40 wt. %, 50 wt. %, 60 wt. %, or 70 wt. %. Unless specified otherwise, as used herein, a given weight percentage (wt. %) of a component of the polymerizable composition is relative to the total weight of all polymerizable ingredients and IPN polymers (as described further below) in the polymerizable composition. The weight of the polymerizable composition contributed by components, such as diluents, that do not incorporate into the final contact lens product are not included in the wt. % calculation.

In a specific example, the polymerizable composition comprises a hydrophilic vinyl monomer. As used-herein, a "hydrophilic vinyl monomer" is any siloxane-free (i.e. contains no Si—O groups) hydrophilic monomer having a polymerizable carbon-carbon double bond (i.e., a vinyl group) present in its molecular structure that is not part of an acryl group, where the carbon-carbon double bond of the vinyl group is less reactive than the carbon-carbon double bond present in a polymerizable methacrylate group under free radical polymerization. As used herein, the term "acryl group" refers to the polymerizable group present in acrylate, methacrylates, acrylamides, etc. Thus, while carbon-carbon double bonds are present in acrylate and methacrylate groups, as used herein, such polymerizable groups are not considered to be vinyl groups. Further, as used herein, a monomer is "hydrophilic" if at least 50 grams of the monomer are fully soluble in 1 liter of water at 20° C. (i.e., ~5% soluble in water) as determined visibly using a standard shake flask method. In various examples, the hydrophilic vinyl monomer is N-vinyl-N-methylacetamide (VMA), or N-vinyl pyrrolidone (NVP), or 1,4-butanediol vinyl ether (BVE), or ethylene glycol vinyl ether (EGVE), or diethylene glycol vinyl ether (DEGVE), or any combination thereof. In one example, the polymerizable composition comprises at least 10 wt. %, 15 wt. %, 20 wt. %, or 25 wt. % up to about 45 wt. %, 60 wt. %, or 75 wt. % of a hydrophilic vinyl monomer. As used herein, a given weight percentage of a particular class of component (e.g., hydrophilic vinyl monomer, siloxane monomer, or the like) in the polymerizable composition equals the sum of the wt. % of each ingredient in the composition that falls within the class. Thus, for example, a polymerizable composition that comprises 5 wt. % BVE and 25 wt. % NVP and no other hydrophilic vinyl monomer, is said to comprise 30 wt. % hydrophilic vinyl monomer. In one example, the hydrophilic vinyl monomer is a vinyl amide monomer. Exemplary hydrophilic vinyl amide monomers are VMA and NVP. In a specific example, the polymerizable composition comprises at least 25 wt. % of a vinyl amide monomer. In a further specific example, the polymerizable composition comprises from about 25 wt. % up to about 75 wt. % of VMA or NVP, or a combination thereof. Additional hydrophilic monomers that may be included in the polymerizable composition are N,N-dimethylacrylamide (DMA), 2-hydroxyethyl methacrylate (HEMA), ethoxyethyl methacrylamide (EOEMA), ethylene glycol methyl ether methacrylate (EGMA), and combinations thereof.

In addition, or as an alternative to a hydrophilic monomer, the polymerizable composition may comprise a non-polymerizable hydrophilic polymer, which results in a polymeric lens body comprising an interpenetrating polymer network (IPN) with the non-polymerizable hydrophilic polymer interpenetrating the silicone hydrogel polymer matrix. In this example, the non-polymerizable hydrophilic polymer is referred to as an IPN polymer, which acts as an internal wetting agent in the contact lens. In contrast, polymer chains within the silicone hydrogel network that form by polymerization of monomers present in the polymerizable composition are not considered to be IPN polymers. The IPN polymer may be a high molecular weight hydrophilic polymer, for example from about 50,000 to about 500,000 Daltons. In a specific example, the IPN polymer is polyvinylpyrrolidone (PVP). In other examples, the polymerizable composition is substantially free of polyvinyl pyrrolidone or other IPN polymer. As an example, the IPN polymer may comprise one or more positively charged sites, such as a tertiary amine group and/or a quaternary amine group, that can form ionic complexes with the oleic acid to increase uptake of the oleic acid by the polymeric lens body and/or sustain its release.

As an option, one or more non-silicon containing hydrophobic monomers can be present as part of the polymerizable composition. A hydrophobic monomer can be understood to be any monomer for which 50 grams of the monomer are not visibly fully soluble in 1 liter of water at 20° C. using a standard shake flask method. Examples of suitable hydrophobic monomers include methyl acrylate, or ethyl acrylate, or propyl acrylate, or isopropyl acrylate, or cyclohexyl acrylate, or 2-ethylhexyl acrylate, or methyl methacrylate (MMA), or ethyl methacrylate, or propylmethacrylate, or butyl acrylate, or 2-hydroxybutyl methacrylate, or vinyl acetate, or vinyl propionate, or vinyl butyrate, or vinyl valerate, styrene, or chloroprene, or vinyl chloride, or vinylidene chloride, or acrylonitrile, or 1-butene, or butadiene, or methacrylonitrile, or vinyltoluene, or vinyl ethyl ether, or perfluorohexylethylthiocarbonylaminoethyl methacrylate, or isobornyl methacrylate (IBM), or trifluoroethyl methacrylate, or hexafluoroisopropyl methacrylate, or tetrafluoropropyl methacrylate, or hexafluorobutyl methacrylate, or any combinations thereof.

The hydrophobic monomer, if used, can be present in the reaction product of the polymerizable composition in amounts of from 1 wt. % to about 30 wt. %, such as from 1 wt. % to 25 wt. %, from 1 wt. % to 20 wt. %, from 1 wt. % to 15 wt. %, from 2 wt. % to 20 wt. %, from 3 wt. % to 20 wt. %, from 5 wt. % to 20 wt. %, from 5 wt. % to 15 wt. %, from 1 wt. % to 10 wt. %, based on the total weight of the polymerizable composition.

The amount of oleic acid that can be taken up by the polymeric lens body can be increased by including a cationic monomer in the polymerizable composition. For example, one or more monomers containing a tertiary amine group, and/or a quaternary amine group can be included in the polymerizable composition. The resulting polymeric lens body contains positively charged groups that facilitate uptake and/or sustained release of the oleic acid by the polymeric lens body.

In one example the polymerizable composition comprises at least one acyclic tertiary amine monomer in amounts of from 2 wt. % to about 15 wt. %, such as from 2 wt. % to 14 wt. %, from 2 wt. % to 12 wt. %, from 2 wt. % to 10 wt. %, from 2 wt. % to 7 wt. %, from 2 wt. % to 5 wt. %, from 5 wt. % to 15 wt. %, from 6 wt. % to 15 wt. %, from 8 wt. % to 15 wt. %, based on the total weight of the polymerizable composition. With respect to the acyclic tertiary amine monomer, as used herein, the at least one acyclic tertiary amine monomer can be understood to comprise a single acyclic tertiary amine monomer, or to comprise an acyclic tertiary amine monomer component composed of two or more acyclic tertiary amine monomers, such as two, three, or four or more. The acyclic tertiary amine monomer is a monomer in which the nitrogen of the tertiary amine group is not part of a ring structure, though the monomer may contain a ring structure (e.g. N-(2-Aminoethyl) aminomethyl styrene). The term "tertiary amine group" is understood to refer to a nitrogen atom directly bonded to three carbon atoms provided none of the carbon atoms is part of a carbonyl group.

Exemplary acyclic tertiary amine monomers include, but are not limited to, 2-(dimethylamino)ethyl acrylate, or 2-(diethylamino)ethyl acrylate, or 3-(dimethylamino)propyl acrylate, or 3-(diethylamino)propyl acrylate, or 2-(dimethylamino)ethyl methacrylate, or 2-(diethylamino)ethyl methacrylate, or 3-(dimethylamino)propyl methacrylate, or 3-(diethylamino)propyl methacrylate, or N-(2-(dimethylamino)ethyl) acrylamide, or N-(2-(diethylamino)ethyl) acrylamide, or N-(3-(dimethylamino)propyl) acrylamide, or N-(3-(diethylamino)propyl) acrylamide, or N-(2-(dimethylamino)ethyl) methacrylamide, or N-(2-(diethylamino)ethyl) methacrylamide, or N-(3-(dimethylamino)propyl) methacrylamide, or N-(3-(diethylamino)propyl) methacrylamide, or 3-(diethylamino)propyl vinyl ether, or 3-(dimethylamino)propyl vinyl ether or any combinations thereof.

A more specific example of the acyclic tertiary amine monomer is 2-(diethylamino)ethyl methacrylate, which can be present in an amount of from 0.1 wt. % to 15 wt. % or from 1 wt. % to 10 wt. % in the polymerizable composition (based on the total weight of the polymerizable composition).

In general, the acyclic tertiary amine monomer (and once part of the polymeric lens body) will form charged sites in lower pH and/or lower ionic strength solutions, e.g., pH of below 8.0 or below 7 or in acidic conditions, such as a pH of 6 or lower (e.g., pH of from 4 to 6). In these conditions, the acyclic tertiary amine groups are protonated forming positively charged sites in the lens material. These positively charged sites can form ionic complexes with the oleic acid.

Advantageously, one or more tertiary amine monomer is included in the polymerizable composition to provide a polymeric lens body with a cationic content of from about 1.0%, or 2.0% or 3.0% up to about 5.0%, 7.0%, or 10.0%. As used "cationic content" is a value determined by Formula I:

$$\Sigma(a_{n1} \times b_{n1}/c_{n1}) \times 157 = \% \text{ cationic content} \quad (I)$$

where $a_{n1}$ is the weight percentage, as defined below, of cationic monomer n1 used in the monomer mixture, $b_{n1}$ is the number of tertiary amine groups on monomer n1, and $c_{n1}$ is the molecular weight of the tertiary amine-containing monomer n1. If more than one tertiary amine-containing monomer is used in the polymerizable composition, the % tertiary amine content of the resulting polymeric lens body is the sum of the % ionic content provided by each tertiary amine-containing monomer (i.e. n1, n2, etc.). The weight percentage of the tertiary amine containing monomer n1 in the polymerizable composition is relative to the weight of all components of the monomer mixture that incorporate into the hydrogel. In other words, ingredients of the monomer mixture that do not incorporate into the final hydrogel product, such as diluents that are removed from the hydrogel during the manufacturing process, are not included in the weight percent determination. Formula I adjusts for differences in molecular weight and charge relative to 2-(dimethylamino)ethyl methacrylate, an exemplary tertiary amine-containing monomer, which has a molecular weight of 157 and one tertiary amine group.

The polymerizable composition may additionally comprise at least one cross-linking agent. As used herein, a "cross-linking agent" is a molecule having at least two polymerizable groups. Thus, a cross-linking agent can react with functional groups on two or more polymer chains so as to bridge one polymer to another. The cross-linking agent may comprise an acryl group or a vinyl group, or both an acryl group and a vinyl group. In certain examples, the cross-linking agent is free of siloxane moieties, i.e., it is a non-siloxane cross-linking agent. A variety of cross-linking agents suitable for use in silicone hydrogel polymerizable compositions are known in the field (see, e.g., U.S. Pat. No. 8,231,218, incorporated herein by reference). Examples of suitable cross-linking agents include, without limitation, lower alkylene glycol di(meth)acrylates such as triethylene glycol dimethacrylate and diethylene glycol dimethacrylate; poly(lower alkylene) glycol di(meth)acrylates; lower alkylene di(meth)acrylates; divinyl ethers such as triethyleneglycol divinyl ether, diethyleneglycol divinyl ether, 1,4-butanediol divinyl ether and 1,4-cyclohexanedimethanol divinyl ether; divinyl sulfone; di- and trivinylbenzene; trimethylolpropane tri(meth)acrylate; pentaerythritol tetra(meth)acrylate; bisphenol A di(meth)acrylate; methylenebis(meth)acrylamide; triallyl phthalate; 1,3-Bis(3-methacryloxypropyl)tetramethyldisiloxane; diallyl phthalate; and combinations thereof.

As will be appreciated by those skilled in the art, the polymerizable composition may comprise additional polymerizable or non-polymerizable ingredients conventionally used in contact lens formulations such as one or more of a polymerization initiator, a UV absorbing agent, a tinting agent, an oxygen scavenger, a chain transfer agent, or the like. In some examples, the polymerizable composition may include an organic diluent in an amount to prevent or minimize phase separation between the hydrophilic and hydrophobic components of the polymerizable composition, so that an optically clear lens is obtained. Diluents commonly used in contact lens formulations include hexanol, ethanol, and/or other alcohols. In other examples, the polymerizable composition is free or substantially free (e.g., less than 500 ppm) of an organic diluent. In such examples, the use of siloxane monomers containing hydrophilic moieties such as polyethylene oxide groups, pendant hydroxyl groups, or other hydrophilic groups, may make it unnecessary to include a diluent in the polymerizable composition. Non-limiting examples of these and additional ingredients that may be included in the polymerizable composition are provided in U.S. Pat. No. 8,231,218.

Non-limiting examples of silicone hydrogels that may be used include comfilcon A, fanfilcon A, stenfilcon A, senofilcon A, senofilcon C. somofilcon A, narafilcon A, delefilcon A, narafilcon A, lotrafilcon A, lotrafilcon B, balafilcon A, samfilcon A, galyfilcon A, and asmofilcon A.

A specific example of a silicone hydrogel contact lens of the present invention is one that is based on a polymerizable composition comprising from 25 wt. % to 55 wt. % of a siloxane monomer(s), from 30 wt. % to 55 wt. % of a vinyl monomer selected from NVP, VMA, or combinations thereof, and optionally from about 1 wt. % to about 20 wt. % of a hydrophilic monomer selected from N,N-dimethylacrylamide (DMA), 2-hydroxyethyl methacrylate (HEMA), ethoxyethyl methacrylamide (EOEMA), or ethylene glycol methyl ether methacrylate (EGMA), or any combination thereof, and optionally from about 1 wt. % to about 20 wt. % of a hydrophobic monomer selected from methyl methacrylate (MMA), isobornyl methacrylate (IBM), or 2-hydroxybutyl methacrylate (HOB) or any combination thereof. Silicone hydrogel materials made from this specific embodiment of polymerizable composition include stenfilcon A, comfilcon A, somofilcon A, fanfilcon A, and enfilcon A. The above base polymerizable composition is further modified to additionally comprise from 0.1 wt. % to 15 wt. % of at least one acyclic tertiary amine, such as, for example, 2 wt. % to 10 wt. % of 2-(dimethylamino)ethyl methacrylate and cured to provide a cationic polymeric lens body.

Conventional methods can be used to manufacture the contact lens of the invention. As an example, a polymerizable composition for a silicone hydrogel composition is dispensed into a female mold member having a concave surface that defines the front surface of the contact lens. A male mold member having a convex surface that defines the back surface of the contact lens, i.e. the cornea-contacting surface, is combined with the female mold member to form a contact lens mold assembly that is subjected to curing conditions, such as UV or thermal curing conditions, under which the curable composition is formed into a polymeric lens body. The female and male mold members can be non-polar molds or polar molds. The mold assembly is disassembled (i.e. demolded) and the polymeric lens body is removed from the mold and contacted with a solvent, for instance, an organic solvent, such as ethanol, to extract unreacted components from the lens body. After extraction, the lens body is hydrated in one or more hydration liquids such as water or an aqueous solution and packaged. Exemplary methods of manufacturing silicone hydrogel contact lenses are described in U.S. Pat. No. 8,865,789.

The oleic acid is typically loaded into the polymeric lens during the extraction step. Generally, after curing, the polymeric lens body is swelled in an extraction solvent, such as ethanol, which contains the oleic acid. When the extracted polymeric lens body is subsequently placed in a hydration solution, such as deionized water, the extraction solvent is removed, and the oleic acid remains adhered to the polymeric lens body.

Examples of the extraction solvents and hydration liquids used in an extraction and hydration process can consist of denatured ethanol, a 50/50 (by vol) mixture of denatured ethanol and deionized water, and deionized water. As an example, the extraction and hydration process can involve at least one extraction step in denatured ethanol followed by a 50:50 mixture of ethanol water followed by at least one hydration step in deionized water, and wherein each extraction and hydration step can last from about 15 minutes to about 3 hours at a temperature of from about 20° C. and to about 30° C. An extraction solvent can contain the oleic acid to achieve uploading of the oleic acid to the polymeric lens body. In some examples, such as when the polymeric lens body contains cationic groups, the amount of oleic acid taken up by the polymeric lens body may be increased by adjusting the pH of the extraction solvent to have a pH of 7 or lower, such as from about 4 to about 6.5.

Any extraction solvent used as an uploading solution for the oleic acid can contain a concentration of oleic acid of at least 50 ppm. This concentration can be at least 100 ppm, at least 250 ppm, at least 500 ppm, at least 750 ppm, at least 1000 ppm, at least 1250 ppm, at least 1500 ppm, at least 1750 ppm, or at least 2000 ppm of oleic acid. In one example, the concentration of oleic acid in the extraction solvent is from about 500 to about 2000 ppm.

In some examples, the oleic acid, once adhered to the polymeric lens body is stable and does not substantially release from the polymeric lens body or degrade during autoclaving of the sealed contact lens package that contains the unworn silicone hydrogel contact lens in a packaging solution, or during storage in its packaging solution, but does release during lens wear. Thus, the packaging solution that the contact lens is immersed in, before autoclaving, or immediately after autoclaving, or after 1 day thereafter, or after 30 days thereafter, or after 60 days thereafter, or after 120 days thereafter has less than 10 ppm oleic acid released into the packaging solution from the contact lens or less than 5 ppm or less than 1 ppm or 0 ppm released from the contact lens into the packaging solution. Whether the oleic acid is released from a contact lens during autoclave or storage can be determined by testing for the presence of the oleic acid in the packaging solution using liquid chromatography-mass spectrometry (LCMS). or other suitable analytical method.

As part of the present invention, the contact lens can be sealed in a contact lens package. The packaging solution sealed within the contact lens package may be any conventional contact-lens compatible solution. In one example, the packaging solution comprises, consists, or consists essentially, of an aqueous solution of a buffer, and/or a tonicity agent. In another example, the packaging solution contains additional agents such as one or more additional antimicrobial agents, and/or a comfort agent, and/or a hydrophilic polymer, and/or a surfactant and/or other beneficial agent. In some examples, the packaging solution may comprise polysaccharides (e.g. hyaluronic acid, hydroxypropyl methylcellulose, hydroxypropyl cellulose, hydroxyethyl cellulose, etc.) or other high molecular weight polymers, such as polyvinyl pyrrolidone, which are commonly used as comfort polymers or thickening agents in ophthalmic solutions and contact lens packaging solutions. In other examples, the packaging solution may comprise an ophthalmic drug. The packaging solution can have a pH in the range of about 6.8 or 7.0 up to about 7.8 or 8.0. In one example, the packaging solution comprises phosphate buffer or borate buffer. In another example, the packaging solution comprises a tonicity agent selected from sodium chloride or sorbitol in an amount to maintain osmolality in the range of about 200 to 400 mOsm/kg, and typically from about 270 mOsm/kg up to about 310 mOsm/kg.

With respect to the contact lens package, this package can include or comprise a plastic base member comprising a cavity configured to retain the contact lens and packaging solution and a flange region extending outwardly around the cavity. A removable foil is attached to the flange region to provide a sealed contact lens package. Such contact lens packages, which are commonly referred to as "blister packs", are well-known in the art (see e.g. U.S. Pat. No. 7,426,993).

It will be appreciated that conventional manufacturing methods can be used to manufacture the sealed contact lens package. In a method of manufacturing a contact lens package, the method can include the step of placing an unworn contact lens and a contact lens packaging solution in a receptacle, placing a cover on the receptacle, and sealing the cover on the receptacle. Generally, the receptacle is configured to receive a single contact lens and an amount of packaging solution sufficient to completely cover the contact lens, typically about 0.5-1.5 ml. The receptacle may be made from any suitable material, such as glass or plastic. In one example, the receptacle comprises a plastic base member comprising a cavity configured to retain the contact lens and packaging solution and a flange region extending outwardly around the cavity, and the cover comprises a removable foil attached to the flange region to provide the sealed contact lens package. The removable foil may be sealed by any conventional means such as heat sealing or gluing. In another example, the receptacle is in the form of a plastic base member comprising a plurality of threads and the cover comprises a plastic cap member comprising a compatible set of thread for engagement with the threads of the base member thereby providing a resealable cover. It will be appreciated that other types of packaging can also be used to provide a resealable package. For example, the contact lens package may comprise a plastic cover comprising features that engage with compatible features of the receptacle to form an interference fit. The method of manufacturing the sealed contact lens package may further comprise sterilizing the unworn contact lens by autoclaving the sealed contact lens package. Autoclaving generally involves subjecting the sealed contact lens package to temperatures of at least 121° C. for at least 20 minutes.

The contact lens can be provided unworn (i.e. a new contact lens, not having been previously used by a patient), immersed in the packaging solution and sealed in a package. The package may be a blister package, glass vial, or other appropriate container. The package comprises a base member having a cavity for accommodating a packaging solution and an unworn contact lens. The sealed package may be sterilized by sterilizing amounts of radiation, including heat or steam, such as by autoclaving, or by gamma radiation, e-beam radiation, ultraviolet radiation, etc.

In a specific example, the packaged contact lens is sterilized by autoclaving.

The final product can be a sterile, packaged contact lens (e.g. silicone hydrogel contact lens) having ophthalmically-acceptable surface wettability.

The oleic acid-releasing hydrogel contact lens described herein can be used to correct vision of a symptomatic contact lens wearer. For example, the oleic acid-releasing hydrogel contact lens contact lens of the invention can increase the duration of comfortable contact lens wearing time in a symptomatic contact lens wearer. References herein to a "symptomatic contact lens wearer" or "symptomatic subject" refers to a lens wearer that is classified as symptomatic using the CLDEQ-8 as described by Chalmers et al (see Chalmers et al., *Contact Lens Dry Eye Questionnaire-8 (CLDEQ-8) and opinion of contact lens performance*. Optom Vis Sci 2012; 89(10): 1435-1442.).

The oleic acid-releasing hydrogel contact lens described herein can be worn by a symptomatic contact lens wearer to reduced lens awareness and/or result in fewer "lens awareness events" during the day compared to a control lens or the symptomatic contact lens wearer's habitual lenses. References herein to a "control lens" refer to a contact lens that contains no oleic acid but is otherwise identical to the oleic acid-releasing lens to which it is being compared. A reduction in lens awareness and/or lens awareness events during contact lens wear can be determined using a "lens awareness logger" as described by Read et al. (see Read et al., *Monitoring ocular discomfort using a wrist-mounted electronic logger*. Contact Lens and Anterior Eye Vol. 43 (2020) 476-483.

A symptomatic contact lens wearer may wear an oleic acid-releasing lens of the invention during the entire time of lens wear. In other examples, the symptomatic contact lens wearer wears an initial contact lens that does not contain oleic acid for four or more hours and replaces the initial contact lens with an oleic acid-releasing hydrogel contact lens of the invention to increase end-of-day comfort of the symptomatic contact lens wearer.

The following Examples illustrate certain aspects and advantages of the present invention, which should be understood not to be limited thereby.

EXAMPLE 1

Oleic Acid-Loaded Stenfilcon A Contact Lenses

Silicone hydrogel contact lenses were prepared by curing the formulation for stenfilcon A in polypropylene contact lens molds. The cured stenfilcon A was removed from the molds and extracted by immersing them for 215 minutes in ethanol (EtOH) containing oleic acid (88.5% purity; Croda Internatinal Plc) in the concentrations shown in Table I. The lenses were removed from the EtOH and washed in a mixture of 50/50 (vol) EtOH/water for approximately 30 minutes followed by three exchanges of DI water for approximately 6 minutes, 30 minutes, and 30 minutes, respectively. The lenses were packaged in the plastic blisters used for MyDay® brand contact lenses with about 1.5 ml of a packaging solution comprising phosphate buffered saline (PBS).

The amount of oleic acid (OA) in each lens (n=3) was determined by extracting the lens with isopropanol (IPA) and measuring oleic in the extract by liquid chromatography-mass spectrometry (LCMS). Briefly, each lens was removed from its blister pack, lightly blotted to remove excess packaging solution, and placed in a 20 mL glass vial containing 10 mL 100% isopropanol (IPA). The vials were placed on a bench top shaker at 300 rpm overnight (~16 hours) at room temperature. For stenfilcon A, a single overnight extraction step is sufficient to extract substantially all the oleic acid from the lense. Silicone hydrogel lens materials that are more hydrophobic may require a second overnight extraction in order to extract all the oleic acid, in which case the IPA from the first extraction step is removed and replaced with 3 mL fresh IPA and shaken overnight at 300 rpm at room temperature. The amount of oleic acid in the IPA extract from each lens is determined by liquid chromatography-mass spectrometry (LCMS). The oleic acid loading concentrations and average oleic acid uptake amount per lens are shown in Table 1.

TABLE 1

| Lens | OA loading concentration | Average amount of OA/lens |
|---|---|---|
| A | 0.25 mg/mL | 32 µg |
| B | 0.75 mg/mL | 90 µg |
| C | 1.5 mg/mL | 180 µg |

Example 2

Clinical Results

Contact lenses B and C from Example 1 were worn by contact lens wearers (n=3 for each lens). Lens C, having the highest loading concentration of oleic acid, caused an initial mild burning/stinging sensation upon lens insertion, which soon subsided. Using the EtOH release method described in Example 3, it was determined that Lens C releases approximately 22 µg oleic acid in the first hour. Contact Lens B from Example 1, which was determined to release approximately 12 µg oleic acid in the first hour (using the release method described in Example 3), caused no burning/stinging upon initial insertion, and was selected for further clinical evaluation. Lens B was determined to sustain release of oleic acid for about 6 hours using the release method described in Example 3.

Twenty-five subjects were enrolled in a two-day, bilateral, 10-hour cross-over study. Twelve of the subjects were classified as symptomatic contact lens wearers, reporting a rating of ≤85 out of 100 on a visual analogue scale for dryness (0=Very dry, 100=No dryness at all) and/or discomfort (0=Very poor comfort, 100=Excellent comfort) after seven hours of habitual lens wear on both the study days. Thirteen subjects were classified as asymptomatic contact lens wearers, reporting a rating of >85 out of 100 on a visual analogue scale for dryness (0=Very dry, 100=No dryness at all) and/or discomfort (0=Very poor comfort, 100=Excellent comfort) on either study day with their habitual contact lenses. All subjects were asked to wear their habitual lenses for 7 hours. The lenses were then replaced with Lens B from Example 1 (Test lens) or MyDay® brand (Control) lenses, which the subjects wore for three hours. Nine out of twelve symptomatic subjects preferred the Test lens, with the remaining three symptomatic subjects preferring the Control. Five of the asymptomatic subjects preferred the Control lens, three preferred the Test lens with the remaining 5 asymptomatic subjects having no preference between the lenses. The data suggest that the oleic acid-containing lenses are overwhelmingly preferred among symptomatic subjects. For symptomatic subjects who reported a preference for the Test lens, six subjects reported less lens awareness and three subjects reported less dryness.

Example 3

Determination of Oleic Acid Release Profile from a Silicone Hydrogel Contact Lens When artificial tear film (ATF) was used as an in vitro release media, the amount of oleic acid released by the Lens B and Lens C lenses of Example 1 after 1 hour release were not statistically different, with Lens C having an average of 24.6 µg oleic acid release after 1 hour, and Lens B having an average of 24.1 µg oleic acid release after 1 hour. There was, however, statistically significant differentiation between the Lens B and Lens C release profiles at the 2 hr and 6 hr time points. Because Lens C resulted in stinging upon initial insertion in the clinical study described in Example 2, the in vitro release method described below, which uses 30 vol % EtOH in phosphate buffered saline (PBS) as the release media, was developed to provide a slower and less variable release profile at the initial time points than when ATF is the release media. This method provided statistically significant differentiation between the release profiles of Lens B and Lens C of Example 1 at the 1-hour time point, with Lens B releasing an average 11.9 µg oleic acid and Lens C releasing an average of 22.5 µg oleic acid.

To determine the release profile of oleic acid-containing silicone hydrogel contact lenses, lenses are removed from their package, and excess packaging solution is shaken off the lens. Each lens is transferred to a 6 mL glass file containing 3 mL of 30 vol % ethanol in PBS (referred to herein as the "EtOH release media") at 35° C. The vials are placed on a shaker at 125 rpm in a 35° C. incubator, and at each time point (e.g. 30 min, 1 hr, 2 hr, 3 hr, 4 hr, 6 hr, and 9 hr) 2.5 ml of the EtOH release media is removed from each vial and submitted for analysis, and 2.5 ml of fresh EtOH release media is added back to each vile. At the end of the release experiment, the lenses may be removed from the vials, rinsed in DI water (4×3 sec/rinse) and subjected to IPA extraction as described in Example 1 to determine the amount of oleic acid remaining in the lens.

Example 4

Oleic Acid Release from a Silicone Hydrogel Contact Lens Containing Tertiary Amine Groups Silicone hydrogel contact lenses were prepared as in Example 1, except that the polymerizable formulation for stenfilcon A was modified to replace about 4.5 wt. % of methacrylic acid with about 4.5 wt. % 2-(dimethylamino) ethyl methacrylate. Also, the oleic acid used in this example was obtained from Sigma (99.4% purity) and was used at the concentrations shown in Table 2.

TABLE 2

| Lens | OA loading concentration | Average amount of OA/lens |
|---|---|---|
| D | 0.75 mg/mL | 88 µg |
| E | 1.125 mg/mL | 136 µg |
| F | 1.5 mg/mL | 192 µg |

In vitro release profiles using 30 vol % EtOH in phosphate buffered saline (PBS) as the release media were obtained for lenses D, E and F using the method described in Example 3. Results are shown in Table 3, where the cumulative oleic acid release (from T=0) at each time point is given.

TABLE 3

| Time | Lens D Ave. Cumul. Amt. of OA Release | Lens E Cumul. Amt. of OA Release | Lens F Cumul. Amt. of OA Release |
|---|---|---|---|
| 30 min | 4.5 µg | 5.8 µg | 8.67 µg |
| 1 hr | 10.1 µg | 12.1 µg | 19.2 µg |
| 2 hr | n/a | n/a | 36.3 µg |
| 3 hr | 18.5 µg | 26.1 µg | n/a |
| 4 hr | n/a | n/a | 56.8 µg |
| 6 hr | 25.9 µg | 38.7 µg | 70.4 µg |
| 9 hr | 32.6 µg | 49.5 µg | n/a |

The present invention includes the following aspects/embodiments/features in any order and/or in any combination:

1. An unworn sterile silicone hydrogel contact lens immersed in a packaging solution and sealed in a package, said contact lens comprising:
   (a) a polymeric lens body that is the reaction product of a polymerizable composition comprising at least one siloxane monomer and at least one hydrophilic monomer or at least one hydrophilic polymer or both at least one hydrophilic monomer and at least one hydrophilic polymer; and
   (b) an amount of oleic acid releasably adhered to the polymeric lens body,
   wherein the contact lens has a release profile in a release media consisting of 30 vol % EtOH in PBS comprising release of 2 µg to 25 µg oleic acid at 1 hour.

2. The contact lens of any preceding or following embodiment/feature/aspect, wherein the amount of oleic acid releasably adhered to the polymeric lens body is from about 25 µg to about 500 µg.

3. The contact lens of any preceding or following embodiment/feature/aspect, wherein the amount of oleic acid releasably adhered to the polymeric lens body is from about 100 µg to about 300 µg.

4. The contact lens of any preceding or following embodiment/feature/aspect, wherein the contact lens sustains release of oleic acid for at least 8 hours in the release media.

5. The contact lens of any preceding or following embodiment/feature/aspect, wherein the release profile comprises a cumulative release of from 2 µg to 10 µg oleic acid at 30 minutes, a cumulative release of 7 to 20 µg oleic acid at 1 hour, a cumulative release of 15 µg to 45 µg oleic acid at 3 hours, a cumulative release of 25 µg to 65 µg oleic acid at 6 hours, and a cumulative release of 35 µg to 75 µg oleic acid at 9 hours.

6. The contact lens of any preceding or following embodiment/feature/aspect, wherein the release profile comprises release of from 3 to 20 µg oleic acid per hour for at least 9 hours in the release media.

7. The contact lens of any preceding or following embodiment/feature/aspect, wherein the polymeric lens body comprises tertiary amine groups that facilitate sustained release of the oleic acid.

8. The contact lens of any preceding or following embodiment/feature/aspect, wherein the polymeric lens body has a cationic content of from about 1.0% to about 10.0%.

9. The contact lens of any preceding or following embodiment/feature/aspect, wherein the polymerizable composition comprises an acyclic tertiary amine monomer.

10. The contact lens of any preceding or following embodiment/feature/aspect, wherein the polymerizable composition comprises 2-(dimethylamino)ethyl methacrylate (DMAEMA).

11. The contact lens of any preceding or following embodiment/feature/aspect, wherein the package comprises:
   (a) a base member having a cavity that retains the packaging solution; and
   (b) a cover that forms a liquid-tight seal with the base member.

12. A method of making the silicone hydrogel contact lens of any preceding or following embodiment/feature/aspect, said method comprising a) polymerizing said polymerizable composition in a contact lens mold to obtain the polymeric lens body, b) removing the polymeric lens body from said contact lens mold, c) extracting the polymeric lens body in an organic solvent comprising from about 500 ppm to about 2000 ppm oleic acid, d) hydrating the polymeric lens body in a hydration liquid to obtain the silicone hydrogel contact lens, e) sealing said silicone hydrogel contact lens with packaging solution in a package, and e) autoclaving said package.

13. Use of the silicone hydrogel contact lens of any preceding or following embodiment/feature/aspect, for correcting vision of a symptomatic contact lens wearer.

14. A method for correcting vision of a symptomatic contact lens wearer, said method comprising wearing the silicone hydrogel contact lens of any preceding or following embodiment/feature/aspect, by the symptomatic contact lens wearer.

15. The use of any preceding or following embodiment/feature/aspect, wherein the symptomatic contact lens wearer has an increased duration of comfortable contact lens wearing time compared to a control lens.

16. The use of any preceding or following embodiment/feature/aspect, wherein the symptomatic contact lens wearer has reduced lens awareness and/or fewer "lens awareness events" during the day compared to a control lens.

17. The of any preceding or following embodiment/feature/aspect, wherein the symptomatic contact lens wearer wears an initial contact lens that does not contain oleic acid for four or more hours and replaces the initial contact lens with the silicone hydrogel contact lens to increase end-of-day comfort of the symptomatic contact lens wearer.

The present invention can include any combination of these various features or embodiments above and/or below as set-forth in sentences and/or paragraphs. Any combination of disclosed features herein is considered part of the present invention and no limitation is intended with respect to combinable features.

The disclosure herein refers to certain illustrated examples, it is to be understood that these examples are presented by way of example and not by way of limitation. The intent of the foregoing detailed description, although discussing exemplary examples, is to be construed to cover all modifications, alternatives, and equivalents of the examples as may fall within the spirit and scope of the invention as defined by the additional disclosure.

References herein to "an example" or "a specific example" or "an aspect" or "an embodiment" or similar phrase, are intended to introduce a feature or features of the oleic acid-releasing silicone hydrogel contact lens or components thereof, the sealed contact lens package or components thereof, or method of manufacturing the oleic acid-releasing silicone hydrogel contact lens (depending on context) that can be combined with any combination of previously-described or subsequently-described examples, aspects, embodiments (i.e. features), unless a particular combination of features is mutually exclusive, or if context indicates otherwise. Further, as used in this specification, the singular forms "a," "an," and "the" include plural referents (e.g. at least one or more) unless the context clearly dictates otherwise. Thus, for example, reference to a "contact lens" includes a single lens as well as two or more of the same or different lenses.

The entire contents of all cited references in this disclosure, to the extent that they are not inconsistent with the present disclosure, are incorporated herein by reference.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An unworn sterile silicone hydrogel contact lens immersed in a packaging solution and sealed in a package, said contact lens comprising:
   (a) a polymeric lens body that is the reaction product of a polymerizable composition comprising at least one siloxane monomer, at least one tertiary amine monomer, and at least one hydrophilic monomer or at least one hydrophilic polymer or both at least one hydrophilic monomer and at least one hydrophilic polymer; and
   (b) an amount of oleic acid releasably adhered to the polymeric lens body,
   wherein the contact lens has a release profile in a release media consisting of 30 vol % EtOH in PBS comprising release of 2 µg to 25 µg oleic acid at 1 hour as determined by the method detailed in the examples, and wherein tertiary amine groups of the polymeric lens body facilitate sustained release of the oleic acid, and the polymeric lens body has a cationic content of from about 1.0% to about 10.0%.

2. The contact lens of claim 1, wherein the amount of oleic acid releasably adhered to the polymeric lens body is from about 25 µg to about 500 µg.

3. The contact lens of claim 1, wherein the amount of oleic acid releasably adhered to the polymeric lens body is from about 100 µg to about 300 µg.

4. The contact lens of claim 1, wherein the contact lens sustains release of oleic acid for at least 8 hours in the release media.

5. The contact lens of claim 1, wherein the release profile comprises a cumulative release of from 2 µg to 10 µg oleic acid at 30 minutes, a cumulative release of 7 to 20 µg oleic acid at 1 hour, a cumulative release of 15 µg to 45 µg oleic acid at 3 hours, a cumulative release of 25 µg to 65 µg oleic acid at 6 hours, and a cumulative release of 35 µg to 75 µg oleic acid at 9 hours.

6. The contact lens of claim 1, wherein the release profile comprises release of from 3 to 20 µg oleic acid per hour for at least 9 hours in the release media.

7. The contact lens of claim 1, wherein the polymerizable composition comprises an acyclic tertiary amine monomer.

8. The contact lens of claim 1, wherein the polymerizable composition comprises 2-(dimethylamino)ethyl methacrylate (DMAEMA).

9. The contact lens of claim 1, wherein the package comprises:
   (a) a base member having a cavity that retains the packaging solution; and
   (b) a cover that forms a liquid-tight seal with the base member.

10. A method of making the silicone hydrogel contact lens of claim 1, said method comprising a) polymerizing said polymerizable composition in a contact lens mold to obtain the polymeric lens body, b) removing the polymeric lens body from said contact lens mold, c) extracting the polymeric lens body in an organic solvent comprising from about 500 ppm to about 2000 ppm oleic acid, d) hydrating the polymeric lens body in a hydration liquid to obtain the silicone hydrogel contact lens, e) sealing said silicone hydrogel contact lens with packaging solution in a package, and e) autoclaving said package.

11. A method for correcting vision of a symptomatic contact lens wearer, said method comprising wearing the silicone hydrogel contact lens of claim 1 by the symptomatic contact lens wearer.

12. The method of claim 11, wherein the symptomatic contact lens wearer has an increased duration of comfortable contact lens wearing time compared to a control lens.

13. The method of claim 11, wherein the symptomatic contact lens wearer has reduced lens awareness and/or fewer "lens awareness events" during the day compared to a control lens.

14. The method of claim 11, wherein the symptomatic contact lens wearer wears an initial contact lens that does not contain oleic acid for four or more hours and replaces the initial contact lens with the silicone hydrogel contact lens to increase end-of-day comfort of the symptomatic contact lens wearer.

* * * * *